United States Patent [19]

Stewart et al.

[11] Patent Number: 4,801,613
[45] Date of Patent: * Jan. 31, 1989

[54] BRADYKININ ANTAGONIST PEPTIDES

[75] Inventors: John M. Stewart; Raymond J. Vavrek, both of Denver, Colo.

[73] Assignee: Nova Technology Limited Partnership, Baltimore, Md.

[*] Notice: The portion of the term of this patent subsequent to Sep. 15, 2004 has been disclaimed.

[21] Appl. No.: 63,108

[22] Filed: Jun. 17, 1987

Related U.S. Application Data

[63] Continuation of Ser. No. 744,207, Jun. 13, 1985, Pat. No. 4,693,993.

[51] Int. Cl.$^4$ .................... A61K 37/42; C07K 7/18
[52] U.S. Cl. .................................. 514/14; 514/15; 530/314
[58] Field of Search .................. 514/14, 15; 530/314, 530/327, 328

[56] References Cited

U.S. PATENT DOCUMENTS 4,693,993 9/1987 Stewart et al. .................... 514/14

OTHER PUBLICATIONS

Chem. Abstr., vol. 101, (1984), 84128n.
Chem. Abstr., vol. 88 (1978), 105763w.
Chem. Abstr., vol. 83 (1975), 10811t.
Can. J. Biochen., vol. 57 (1979), 1084–9.
Chem. Abstr., vol. 93 (1980), 186777g.
Chem. Abstr., vol. 91 (1979), 168871.
Chem. Abstr., vol. 94 (1981), 202885.
Chem. Abstr., vol. 81, (1974), 9976.
Chem. Abstr., vol. 83 (1975), 126640.
Chem. Abstr., vol. 89 (1978), 17275.
Chem. Abstr., vol. 92, (1980), 122284.

Primary Examiner—Delbert R. Phillips
Attorney, Agent, or Firm—Breneman & Georges

[57] ABSTRACT

The substitution of the L-Pro at the 7-position of the peptide hormone bradykinin or other substituted analogs of bradykinin with an aromatic amino acid or the D-configuration converts bradykinin agonists into a bradykinin antagonist. The invention further includes additional modifications at other positions within the novel 7-position modified bradykinin antagonists which increase enzyme resistance, antagonist potency and/or specificity of the new bradykinin antagonists. The analogs produced are useful in treating conditions and diseases of the mammal and human body in which an excess of bradykinin or related kinins are produced or injected as by bites into the body.

38 Claims, No Drawings

BRADYKININ ANTAGONIST PEPTIDES

The government has rights in this invention pursuant to Grant Number BNP 2 R37 HL26284-07 awarded by the National Heart, Lung, and Blood Institute of the Department of Health And Human Services.

The invention described herein was made in the course of work under a grant or award from the Department of Health, Education, and Welfare.

CROSS REFERENCE TO RELATED APPLICATION

This invention pertains to new and useful bradykinin antagonist peptides and constitutes a continuation of U.S. application Ser. No. 744,207, filed on June 13, 1985, now U.S. Pat. No. 4,693,993.

FIELD OF THE INVENTION

The invention relates to novel biologically active peptides which act as antagonists of the biological activities of bradykinin, their pharmaceutically acceptable salts, and their application as therapeutic agents.

BACKGROUND OF THE INVENTION

In the 25 years since the sequence of the potent mammalian vasodilator peptide bradykinin was described and synthesized (Boissonnas et al., Experientia 16: 326, 1960) several hundred sequence-related peptide analogs have been synthesized and assayed in biological systems (Schroeder, in Handbook of Experimental Pharmacology, Vol. 25, (Springer Verlag) pp 324–350, 1970) (Stewart, Handbook of Experimental Pharmacology, Vol. 25 (Supplement), (Springer Verlag) pp 227–272, 1979). The objective in these studies was to investigate the varied physiological and pharmacological roles of bradykinin.

Bradykinin, and its physiologically important related peptides kallidin (Lys-bradykinin) and Met-Lys-bradykinin, contract smooth muscle, (for example to produce diarrhea and inflammatory bowel disease and asthma) lower blood pressure, mediate inflammation as in allergies, arthritis and asthma, participate in blood-clotting and complement-mediated reactions in the body, mediate rhinitis (viral, allergic and non-allergic) and are overproduced in pathological conditions such as septic shock, acute pancreatitis, hereditary angioneurotic edema, post-gastrectomy dumping syndrome, carcinoid syndrome, anaphylactic shock, reduced sperm motility, and certain other conditions. The production of bradykinin from the plasma results in pain at the site of the pathological condition, and the overproduction intensifies the pain directly or via stimulation by bradykinin of the activation of the arachidonic acid pathway which produces prostaglandins and leukotrienes, the more distal and actual mediators of inflammation. Literature references describing these actions of bradykinin and related peptides are found in Handbook of Experimetal Pharmacology, Vol. 25, Springer-Verlag, 1970 and Vol. 25 Supplement, 1979.

Bradykinin as discussed has been found to be produced in inflammatory reactions in the intensine provoking contraction of smooth muscle and secretion of fluid and ions. The existence of specific bradykinin receptors in the mucosal lining of the intestine and intestinal smooth muscle is demonstrated by Manning, et al. in *Nature* (229: 256–259, 1982) showing the influence of bradykinin in very low concentrations upon fluid and ion secretion.

The production of bradykinin and associated pain in angina has been studied and reported by Kimura, et al. in *American Heart Journal* (85: 635–647, 1973) and by Staszewska-Barczak, et al. in *Cardiovascular Research* (10:314–327, 1976). The reported action of bradykinin and prostaglandins acting in concert are the natural stimulus for excitation of the sensory receptors signalling the pain of myocardial ischeamia.

Bradykinin and bradykinin-related kinins are not only produced by the animal but may also be injected as a result of stings and bites. It is known that insects such as hornets and wasps inject bradykinin related peptides which also cause pain, swelling and inflammation.

The search for understanding of the mechanism of action of bradykinin, which is essential for the development of useful tools for diagnostic use, and for the development of therapeutic agents aimed at alleviating the intense pain caused by the production and overproduction of bradykinin, has been severely hindered by the lack of specific sequence-related competitive antagonists of bradykinin.

Several non-peptide, non-specific and non-selective antagonists of one or more of the biological activities of bradykinin have been described among compounds as diverse as analgesics and anti-inflammatory substances, which act via the prostaglandin system and not directly on bradykinin biological receptors (Rocha e Silva and Leme, Med. Exp. 8: 287, 1963). These are antihistamines (Gecse et al, J. Pharm. Pharmacol. 21: 544, 1969); bradykinin-antibodies (Grez et al, Eu. J. Pharmacol. 29: 35, 1974); benzodiazepine derivatives (Leme and Rocha e Silva, Br. J. Pharmacol. 25: 50, 1965); high molecular weight ethylene oxide polymers (Wilkens and Back, Arch. Intl. Pharmacodynam. 209: 305, 1974); gallic acid esters (Posati et al., J. Agri. Food Chem. 18: 632, 1970) and serotonin inhibitors (Gomazkon and Shimkovich, Bull. Exptl. Biol. Med. 80: 6, 1975). None of these individual compounds or classes of compounds specifically inhibit bradykinin.

Heptyl esters of various amino acid-containing substances, such as single basic amino acids (ie. Arg and Lys) (Gecse, Adv. Exptl. Biol. Med. 70: 5, 1976), the dipeptide PheGly (Gecse et al, Int. Aech. Allergy 41: 174, 1971), and of analogs of C- terminal peptide fragments of bradykinin (ie. Pro-Phe-Arg)(Claesson et al., Adv. Exptl. Med. Biol. 120B: 691, 1979) have been reported as anti-bradykinin substances. When tested in bradykinin assay systems they prove to be weak partial agonists/antagonists, depending on the dose, with little specificity for inhibiting bradykinin action.

Preparations of damaged vascular tissue have been reported to respond to bradykinin analogs which lack the C-terminal Arg residue, but not to bradykinin itself, and analogs of these des-Arg$^9$-bradykinins have been developed as antagonists of this non-physiological activity of bradykinin. These antagonists have no significant bradykinin-like agonist effects, nor any antagonist effect on any of the physiologically significant kinin-responding systems (Regoli and Barabe, Pharmacol. Revs. 32:1, 1980).

Several bradykinin analogs containing the O-methyl ether of Tyr residues at positions 5 and/or 8 have been reported to produce mixed agonist/antagonist activity on isolated uteri of galactosemic rats, but not on normal rats. The antagonism was not reliably reproducible in these animals (Steward and Woolley, in Hypotensive peptides, Springer Verlag, pp 23-33, 1966).

Other changes in the bradykinin molecule have been additions of amino acids at the N-terminal end which affect the rate of enzymatic degradation of bradykinin in vivo.

The half life of bradykinin in the systemic circulation is less than 30 seconds (S. H. Ferreira & J. R. Vane, Br. J. Pharmacol. Chemotherap. 30:417, 1967). Bradykinin is completely destroyed (98-99% destruction) on a single passage through the pulmonary circulation (J. Roblero, J. W. Ryan and J. M. Stewart, Res. Commun. Pathol. Pharmacol. 6: 207, 1973) as determined in the anesthetized rat by measuring the depressor effects of an agonist following intraaortic (IA) (bypassing the pulmonary circulation) and intravenous (IV) administration. Resistance of bradykinin agonists to pulmonary kininase destruction in vivo is promoted by addition of single (ie, DArg-, DLys-, Lys-) and double (DLys-Lys-) basic amino acid residues to the N-terminal of the bradykinin sequence. The addition of the dipeptide Lys-Lys to the N-terminal of bradykinin agonists confers complete resistance to in vivo destruction on initial passage through the pulmonary circulation (Roblero, Ryan and Stewart, Res. Comm. Pathol. Pharmacol. 6: 207, 1973).

SUMMARY OF INVENTION

The invention relates to the modification of the sequence of the mammalian peptide hormone bradykinin (Arg-Pro-Pro-Gly-Phe-Ser-Pro-Phe-Arg) and pharmaceutically acceptable salts thereof, at the Pro residue at position 7 in a unique manner which, for the first time, produces sequence-related analogues that act as specific and competitive inhibitors of the biological activities of bradykinin. The invention specifically relates to the substitution of the L-Pro at position 7 with aromatic amino acids of the D-configuration, a change which converts bradykinin agonists into antagonists, and includes additional modifications at other positions within the 7-position modified bradykinin antagonist which confer increased antagonist potency, resistance to enzymatic degradation and/or tissue specificity on the D-amino acid-containing bradykinin sequence. More specifically, the invention relates to the peptides of the general formula:

A—Arg—B—C—D—W—X—Y—Z—Arg    Formula I
(0   1   2  3  4  5  6  7  8   9 ) (position number)

wherein

A is a hydrogen atom or single acidic, basic, neutral or aromtic amino acid residue of the D- or L-configuration, such as D-Arg, D-Lys or L-Thi, an N-terminal enzyme protecting group from the group comprising acyl-type protecting groups, aromatic urethane-type protecting groups, alkyl-type protecting groups, or alternately A is a di- or poly-peptide containing amino acids of the D- or L- configuration, such as Lys-Lys, Met-Lys, or Gly-Arg-Met-Lys;

B is an L-pro residue, or other D- or L-cyclic or noncyclic aliphatic amino acid residue, such as L-hydroxyproline, an L-aromatic or substituted aromatic amino acid residue;

C is D- or L-Pro residue, or other cyclic, aliphatic, aromatic or substituted aromatic amino acid residue of the D- or L-configuration;

D is a Gly residue or other aliphatic, aromatic or substituted aromatic amino acid residue of the L-configuration, such as Ala;

W is a Phe residue of the L-configuration, or a substituted Phe or other aliphatic or aromatic amino acid residue, such as Leu, beta-2-thieylalanine (Thi) or 2-pyridyl-alanine (Pal);

X is a Ser residue of the L-configuration, a Gly residue, or other D- or L-aliphatic or aromatic or substituted aromatic amino acid residue, such as pCl-D-Phe or D-Phe;

Y is a D-aromatic amino acid residue, or substituted aromatic amino acid residue, such as D-Phe, beta-(2-thieyl)-D Ala (DThi), beta-(2-pyridyl)-D-Ala (D-Pal), β-2-naphthyl-D Ala (D-Nal), DHis, D-homo-Phe (DhPhe), O-methyl-DTyr (DOMT), D-alphaphenyl-Gly (DPhg), DTrp, DTyr or pCl-DPhe (CDF);

Z is a Phe residue of the L-configuration, or a substituted Phe or other aliphatic or aromatic amino acid residue, such as Leu, Thi or Pal.

In a preferred compound of the general formula I the substituents have the following identity: A=H, B=Pro or Hyp, C=Pro or Hyp, D=Gly, W=Z=Phe or Thi, X=Ser and Y=any aromatic amino acid of the D-configuration.

Salts of peptides of general formula I include salts with HCl, TFA, AcOH, as well as other pharmaceutically acceptable salts.

The following TABLES I and II show substitutions that can be made in the bradykinin polypeptide and the effect of such substitutions. Indicated substitutions of the 0, 1, 2, 3, 5, 7 and 8 amino acid residues of bradykinin yield preferred bradykinin antagonists.

TABLE I
SUBSTITUTIONS IN BRADYDININ ANTAGONISTS

```
                                            DNal
                                            DPNF
              Azt      Azt                  DPhe
              Thz      Thz                  DTyr
              Inip     Inip                 DPal
              DPro     DPro                 DOMT
              ΔPro     ΔPro         Ala     DThi
              Hyp      Hyp          Sar     DAla
                  ↘      ↘          ↗         ↘
              A—Arg—Pro—Pro—Gly—Phe—Ser—Pro—Phe—Arg
                ↗                ↗      ↑         ↑
              DArg              Thi    Gly       Thi
              Lys—Lys           OMT    DPhe      OMT
              DLys—Lys          Pal    CDF       Pal
              Phe, Thi          CLF    DNaL      CLF
                                PNF    DPal      PNF
                                Nal    DThi      Nal
```

Thi = β-(2-Thienyl)alanine
Pal = β-(2-Pyridyl)alanine
Hyp = 4-Hydroxyproline
Azt = Azetidine-2-carboxylic acid
Thz = Thiazolidine-2-carboxylic acid
Inip = Isonipecotic acid
OMT = O—Methyltyrosine
CDF = para-chloro-D-phenylanine
Nal = β-(2-Naphthyl)-alanine
CLF = para-chloro-L-phenylalanine
PNF = para-nitrophenylanine
ΔPro = 2,3-Dehydroproline

TABLE II
CHARACTERISTICS OF BRADYKININ ANTAGONISTS

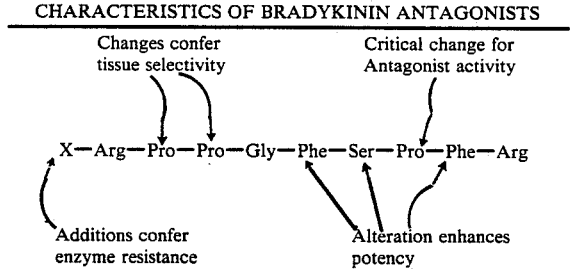

DETAILED DESCRIPTION

The synthesis of the peptides of general Formula I, including derivatization, activation, and coupling of protected amino acid residues, and their purification, and the analytical methods for determining identity and purity are included in the general body of knowledge of peptide chemistry, as described in Houben Weyl "Methoden der Organische Chemie" Vol. 16, parts I and II(1974) for solution-phase synthesis, and in "Solid Phase Peptide Synthesis" by Stewart and Young (1984) for synthesis by the solid-phase method of Merrifield. Any chemist skilled in the art of peptide synthesis can synthesize the peptides of general Formula I by standard solution methods or by manual or automated solid-phase methods.

The symbols and abbreviations used for amino acids, their derivatives and protecting groups, and peptides and their salts are those customarily used in peptide chemistry (Biochem. J. 126: 773,1972, the Journal reference is hereby incorporated by reference.). For convenience several abbreviations are defined in Table III reproduced below. All amino acid residues, except Gly, described in the specification but not the claims are of the L-configuration unless otherwise specified.

TABLE III
ABBREVIATIONS FOR AMINO ACID RESIDUES

| | |
|---|---|
| Aib | alpha-aminoisobutyric acid |
| Azt | azetidine-2-carboxylic acid |
| CDF | para-chloro-D-phenylalanine |
| CLF | para-chloro-L-phenylalanine |
| hPhe | homo-phenylalanine |
| Hyp | 4-hydroxy-proline |
| Inip | isonipecotic acid |
| MDY | O—methyl-D-tyrosine |
| Nal | beta-(2-naphthyl)-alanine |
| ΔPro | 2,3-dehydroproline |
| Pal | beta-(3-pyridyl)-alanine |
| Phg | alpha-phenylglycine |
| Sar | sarcosine |
| Thi | beta-(2-thienyl)-alanine |
| Thz | thiazolidine-2-carboxylic acid |

(all other abbreviations follow the IUPAC standards for amino acid residues)

The following examples are illustrative of compounds of this invention with general formula I and are not limitative. All percentages and ratios are by weight when solids are involved and by volume when only liquids are involved.

EXAMPLE 1

Preparation of Arg-Pro-Pro-Gly-Phe-Ser-DPhe-Phe-Arg (dPhe$^7$-BK).

A mixture of 6.4 gm of tertiary butyloxy carbonyl-(g-paratoluene sulfonyl)-Arg [BOC-Arg(Tos)](15 mMole) and 183 mg of N,N-dimethylaminopyridine (1.5 mMole) was dissolved in a mixture of 20 ml of dimethylformamide (DMF) and 125 ml of dichloromethane (DCM). Fifteen g of hydroxymethyl-polystyrene-divinyl benzene (1% crosslinked, containing 0.74 mMole of free hydroxyl group per g of resin) was added, followed by 60 ml of a 0.25M solution of dicyclohexylcarbodiimide (DCC) in DCM at room temperature. The suspension was stirred at room temperature overnight, filtered, and the resin was washed three times with 60 ml of DCM, three times with 60 ml of methyl alcohol (MeOH), and reswollen in 120 ml of DCM. The coupling of another portion of BOC-Arg(Tos) was conducted on the resin as above. After filtering and washing the resin it was reswollen in 120 ml of DCM, and 2.1 ml of benzoyl chloride and 1.5 ml of triethylamine (Et$_3$N) were added. After stirring the suspension for 30 minutes at room temperature the resin was filtered, washed three times with 60 ml portions of DCM, MeOH, washed three times with 60 ml portion of MeOH and finally washed three times with 60 ml portions of DCM. The resin was air dried to constant weight to give 18.5 gm of BOC-Arg(Tos)-hydroxymethyl-resin, with an actual amino acid content of 0.272 millimoles of Arg per g of resin as determined by quantitative amino acid analysis of a sample of the amino acid resin following hydrolysis (4 hr, 130° C.) in 6N HCL/propionic acid.

The resin, 1.5 gm containing a total of 0.4 mMole of Arg, was placed in the reaction vessel of an automatic solid-phase synthesizer (Beckman model 990) and subjected to one cycle of addition for the coupling of BOC-Phe as follows:

Program A. Standard DCC Coupling:

The resin was washed three times with 20 ml portions of DCM. The resin was then equilibrated with 20 ml of a 1:3 ratio of trifluoroacetic acid (TFA) in DCM containing 0.1% indole for 1.5 minutes. The equilibration was then repeated for 30 minutes. The resin was then washed six times with 20 ml portions of DCM followed by neutralization with a 10% solution of (Et$_3$N) in DCM for one and one half minutes, then the neutralization step was repeated. The resin was washed six times with 20 ml of DCM and then equilibrated with a solution of 1.0 mMole of BOC-Phe in DCM for one and one half minutes. Then four ml of 0.25N DCC in DCM was added and the mixture stirred for two hours. Then the resin was washed three times with 20 ml portions of DCM.

A second cycle of addition was performed according to Program B:

Program B. Reverse Addition:

The procedure of Program A through neutralization and following washes was repeated. Then 1.0 mMole of DCC in 4 ml of DCM was added and the resin and solution were mixed for one and one-half minutes. Then 1.0 mMole of BOC-D-Phe in 12 ml DCM was added and the resin and solution were mixed for two hours. The resin was then washed six times with 20 ml portions of DCM.

The N-Terminal protecting group was removed according to the following sequence:

Program C. Terminal Deprotection:

The procedure of Program A up to the neutralization with triethylamine was repeated. The resin was then washed 6 times with 20 ml portions of ethyl alcohol and the peptide-resin was air dried giving 1.66 gm of DPhe-Phe-Arg-Resin as the trifluoroacetic acid salt.

Synthesis was continued with 410 mg of the DPhe-Phe-Arg-Resin TFA salt. The next residue was added according to PROGRAM D.

Program D. Recouple:

The peptide-resin salt was first washed three times with 20 ml portion of DCM, then neutralized with 10% Et$_3$N DCM for 1.5 minutes. The neutralization step was then repeated and the peptide-resin-salt was washed six times with 20 ml portions of DCM. The peptide-resin was then equilibrated with a solution of 1.0 mMole of BOC-Ser(OBzl) in DMF for 1.5 minutes. Four ml of 025N DCC in DCM was added and mixed with the resin for two hours. The product was washed three times with DCM.

The following amino acid derivatives were added to the growing peptide chain according to the listed Programs: BOC-Phe (A), BOC-Gly (A), BOC-Pro (A), BOC-Pro (A), followed by recouple of BOC-Pro (D), BOC-Arg(Tos)(dissolved in 2 ml DMF+9 ml (DCM), (A), followed by Program C. This gave 530 mg of protected nonapeptide-resin as the TFA salt.

A 510 mg portion of the peptide-resin above was suspended in 10 ml of liquid anhydrous HF containing 1 ml of anisole at −70° C. and stirred 45 min. at 0° C. HF and anisole were removed by vacuum (1 hr water pump, 1 hr vacuum pump), the peptide plus resin was washed three times with 20 ml portions of ethyl ether (Et$_2$O) and the peptide extracted into glacial acetic acid using three 6 ml extractions. The acetic acid solution was lyophilzed to give 185 mg of crude deprotected peptide.

The peptide was purified by countercurrent distribution (CCD) (100 upper phase transfers in a Post CCD apparatus) in the solvent system nBuOH:1% TFA (1:1). The content of the tubes corresponding to the main peptide-containing peak, as determined by the quantitative Sakaguchi reagent, was collected, the solvent evaporated under reduced pressure, the residue dissolved in glacial acetic acid (AcOH) and lyophilized to give 140 mg of peptide with a partition coefficient (k) from the CCD of 5.7. Repeating the countercurrent distribution in the solvent system nBuOH:AcOH:H20 (4:1:5) gave, upon detection and workup as described above, 73 mg of Arg-Pro-Pro-Gly-Phe-Ser-DPhe-Phe-Arg as the TFA salt (k=0.2). Thin layer chromatographs (TLC) on Merck glass precoated silica gel plates in the solvent systems nBuOH:AcOH:H20 (8:3:4) and EtOAc:-pyridine:AcOH:H20 (5:5:1:3) gave Rf(834) of 0.17 and Rf(5513) of 0.36 for the pure peptide, as visualized by the chlorine-tolidine peptide identification spray. Quantitative amino acid analysis (Beckman 120 instrument) after acid hydrolysis (17 hr in sealed glass vials under N$_2$ at 110° C. in 2 ml 6N HCl containing 2 drops 2-mercaptoethanol and 40 microliters of phenol) gave the following ratios of amino acids: Arg(2.12); Pro(1.93); Gly(1.01); Phe(2.98); Ser(0.96).

EXAMPLE 2

Preparation of
Arg-Pro-Pro-Gly-Phe-Ser-DThi-Phe-Arg
(DThi$^7$-BK).

This peptide was prepared by the method in Example 1, except that BOC-beta-2-thienyl-D-Ala (BOC-DThi) was used in place of BOC-DPhe: k(415)=0.24; Arg(2.02), Pro(2.18), Gly(1.00), Phe(1.99), Ser(0.89), Thi(0.99).

EXAMPLE 3

Preparation of
Arg-Pro-Pro-Gly-Phe-Ser-DPal-Phe-Arg (DPal$^7$-BK).

This peptide was prepared by the method in Example 1, except that BOC-2-pyridyl-DAla (BOC-D-Pal) was used in place of BOC-DPhe: k(1:1)=0.22; Arg(2.03), Pro(2.01), Gly(1.02), Phe(1.99), Pal(1.02).

EXAMPLE 4

Preparation of
Arg-Pro-Pro-Gly-Phe-DPhe-DPhe-Phe-Arg
(DPhe$^{6,7}$-BK).

This peptide was prepared by the method in Example 1, except that BOC-DPhe was used in place of BOC-Ser(Bzl): k(415)=1.3; Arg(2.12), Pro(1.94), Gly(1.00), Phe(3.94).

EXAMPLE 5

Preparation of
Arg-Pro-Pro-Gly-Phe-DPhe-CDF-Phe-Arg
(DPhe$^6$CDF$^7$-BK).

This peptide was prepared by the method in Example 1, except that BOC-DPhe was used in place of BOC-Ser(Bzl) and BOC-pCl-D-Phe (BOC-CDF) was used in place of BOC-DPhe: k(415)=0.82; Arg(1.98), Pro(1.93), Gly(0.97), Phe(3.10), CDF(1.02).

EXAMPLE 6

Preparation of
Arg-Pro-Pro-Gly-Thi-Ser-DPhe-Thi-Arg
(Thi$^{5,8}$DPhe$^7$-BK).

This peptide was prepared by the method in Example 1, except that BOC-beta-2-thienyl-Ala (BOC-Thi) was used in the two addition cycles in which BOC-Phe was used in EXAMPLE 1: k(415)=0.21; Arg(1.98), Pro(1.94), Gly(1.04), Phe(1.04), Ser(0.96), Thi(2.05).

EXAMPLE 7

Preparation of
Arg-Pro-Pro-Gly-Thi-Ser-DThi-Thi-Arg
(Thi$^{5,8}$DThi$^7$-BK).

This peptide was prepared by the method in Example 6, except that BOC-DThi was used in place of BOC-DPhe: k(415)=018; Arg(2.07), Pro(2.08), Gly(1.00), Ser(0.93), Thi(2.88).

EXAMPLE 8

Preparation of
Arg-Pro-Pro-Gly-Thi-Ser-DPal-Thi-Arg
(Thi$^{5,8}$DPal$^7$-BK).

This peptide was prepared by the method in Example 6, except that BOC-DPal was used in place of BOC-DPhe: k(1:1)=0.15; Arg(2.00), Pro(2.20), Gly(1.09), Ser(0.89), Thi(1.92), Pal(0.89).

EXAMPLE 9

Preparation of
Arg-Pro-Pro-Gly-Thi-DPhe-CDF-Thi-Arg
(Thi$^{5,8}$DPhe$^6$CDF$^7$-BK).

This peptide was prepared by the method in Example 5, except that BOC-Thi was used in two cycles of addition in place of BOC-Phe: k(415)=0.75; Arg(1.89), Pro(2.08), Gly(1.06), Phe(1.02), Thi(1.88), CDF(1.07).

EXAMPLE 10

Preparation of
DArg-Arg-Pro-Pro-Gly-Phe-Ser-DPhe-Phe-Arg
(DArg$^0$DPhe$^7$-BK).

This peptide was prepared by the method in Example 1, except that one additional cycle using BOC-(Tos)-DArg was performed with Program A followed by terminal deprotection with Program C: k(1:1)=3.55; Arg(2.89), Pro(2.07), Gly(1.02), Phe(3.05), Ser(0.98).

EXAMPLE 11

Preparation of
DArg-Arg-Pro-DPro-Gly-Phe-Ser-DPhe-Phe-Arg
(DArg$^0$DPro$^3$DPhe$^7$-BK).

This peptide was prepared by the method in Example 10, except that BOC-DPro was used in place of BOC-Pro in the first addition of BOC-Pro: k(415)=0.15; Arg(3.12), Pro(1.90), Gly(1.05), Phe(3.02), Ser(0.92).

EXAMPLE 12

Preparation of
Arg-Pro-DPro-Gly-Thi-DPhe-CDF-Thi-Arg
(DPro$^3$Thi$^{5,8}$DPhe$^6$CDF$^7$-BK).

This peptide was prepared by the method in Example 9, except that BOC-DPro was used in place of BOC-Pro in the first addition of BOC-Pro: k(415)=0.18; Arg(2.00), Pro(1.98), Gly(1.04), Phe(0.99), Thi(1.89), PCF(1.11).

EXAMPLE 13

Preparation of
Lys-Lys-Arg-Pro-Pro-Gly-Phe-Ser-DPhe-Phe-Arg
(Lys-Lys-DPhe$^7$-BK).

This peptide was prepared by the method in EXAMPLE 1, except that two additional cycles of addition were performed with BOC-(e-ClZ)Lys, the first with Program D, the second with Program A followed by Program C: k(1:1)=0.52; Arg(2.04), Pro(1.99), Gly(0.96), Phe(3.00), Ser(0.96), Lys(2.01).

EXAMPLE 14

Preparation of
Lys-Lys-Arg-Pro-Pro-Gly-Thi-Ser-DPhe-Thi-Arg
(Lys-Lys-Thi$^{5,8}$DPhe$^7$-BK).

This peptide was prepared by the method in Example 13, except that BOC-Thi was used in place of BOC-Phe in the two cycles of addition of BOC-Phe: k(1:1)=0.33; Arg(1.98), Pro(1.97), Gly(1.01), Phe(1.03), Ser(0.97), Thi(1.96), Lys(2.08).

EXAMPLE 15

Preparation of
DArg-Arg-Pro-Pro-Gly-Thi-Ser-DPhe-Thi-Arg
(DArg$^0$Thi$^{5,8}$DPhe$^7$-BK).

This peptide was produced by the method in Example 6, except that one additional cycle of addition with BOC-(Tos)DArg was performed with Program D, followed by Program C: k(1:1)=2.33; Arg(3.00), Pro(1.99), Gly(0.96), Phe(0.99), Ser(0.95), Thi(2.11).

EXAMPLE 16

Preparation of
DArg-Arg-Pro-DPro-Gly-Thi-Ser-DPhe-Thi-Arg
(DArg$^0$DPro$^3$Thi$^{5,8}$DPhe$^7$-BK).

This peptide was produced by the method in Example 15, except that BOC-DPro was used in place of BOC-Pro in the first addition of BOC-Pro: k(415)=0.22; Arg(2.10), Pro(1.96), Gly(1.05), Phe(0.98), Ser(0.94), Thi(1.96).

EXAMPLE 17

Preparation of
Lys-Lys-Arg-Pro-Hyp-Gly-Phe-Ser-DPhe-Phe-Arg
(Lys-Lys-Hyp$^3$DPhe$^7$-BK).

This peptide was prepared by the method in Example 13, except that BOC-(4-hydroxy)-Pro (BOC-Hyp) was used in place of BOC-Pro in the first addition of BOC-Pro: k(1:1)=0.35; Arg(2.00), Pro(1.03), Gly(1.00), Phe(3.08), Ser(0.94), Lys(1.95), Hy(1.01).

EXAMPLE 18

Preparation of
Arg-Hyp-Pro-Gly-Thi-Ser-DPhe-Thi-Arg
(Hyp$^2$Thi$^{5,8}$DPhe$^7$-BK).

This peptide was produced by the method in EXAMPLE 6, except that BOC-Hyp was used in place of BOC-Pro in the second addition of BOC-Pro, including the recoupling with Program D: k(1:1)=2.45; Arg(2.03), Pro(0.98), Gly(1.06), Phe(1.05), Ser(0.95), Thi(1.97), Hyp(0.95).

EXAMPLE 19

Preparation of
Lys-Lys-Arg-Hyp-Gly-Thi-Ser-DPhe-Thi-Arg
(Lys-Lys-Hyp$^2$Thi$^{5,8}$DPhe$^7$-BK).

This peptide was produced by the method in EXAMPLE 18, except that two additional cycles of addition with BOC-(e-ClZ)Lys were performed, the first with Program D, the second with Program A followed by Program C: k(1:1)=0.27; Arg(2.07), Pro(0.92), Gly(0.99), Phe(1.03), Ser(0.93), Thi(1.92), Lys(2.06), Hyp(1.10).

EXAMPLE 20

Preparation of
Arg-Pro-Hyp-Gly-Thi-Ser-DPhe-Thi-Arg
(Hyp$^3$Thi$^{5,8}$DPhe$^7$-BK).

This peptide was produced by the method in EXAMPLE 6, except that BOC-Hyp was used in place of BOC-Pro in the first addition of BOC-Pro: k(1:1)=2.23; Arg(2.08), Pro(0.98), Gly(1.04), Phe(1.01), Ser(0.99), Thi(1.95), Hyp(0.94).

EXAMPLE 21

Preparation of
DArg-Arg-Pro-Hyp-Gly-Thi-Ser-DPhe-Thi-Arg
(DArg$^0$-Hyp$^3$Thi$^{5,8}$DPhe$^7$-BK).

This peptide was produced by the method in EXAMPLE 20, except that one additional cycle of addition with BOC-(Tos)DArg was done with Program D, followed by Program C: k(1:1)=0.18; Arg (3.01); Pro(1.02), Gly(0.98), Phe(1.02), Ser(0.92), Thi(2.07), Hyp(0.97).

EXAMPLE 22

Preparation of
Arg-Hyp-Hyp-Gly-Thi-Ser-DPhe-Thi-Arg
(Hyp$^{2,3}$Thi$^{5,8}$DPhe$^7$-BK).

This peptide was produced by the method in EXAMPLE 6, except that BOC-Hyp was used in place of BOC-Pro in those cycles where BOC-Pro had been used: k(1:1)=1.56; Arg(2.04), Gly(1.06), Phe(1.02), Ser(1.01), Thi(1.94), Hyp(1.93).

EXAMPLE 23

Preparation of
Arg-Hyp-Hyp-Gly-Thi-DPhe-CDF-Thi-Arg
(Hyp$^{2,3}$Thi$^{5,8}$DPhe$^6$CDF$^7$-BK).

This peptide was produced by the method in Example 9, except that BOC-Hyp was used in place of BOC-Pro in those cycles where BOC-Pro had been used: k(415)=0.89; Arg(2.06), Gly(1.00), Phe(1.03), PCF(1.05), Thi(1.92), Hyp(1.93).

EXAMPLE 24

Preparation of
Arg-Pro-Pro-Gly-Leu-Gly-DPhe-Leu-Arg
(Gly$^6$Leu$^{5,8}$DPhe$^7$-BK).

This peptide was produced by the method in EXAMPLE 1, except that BOC-Leu was used in place of BOC-Phe in those cycles where BOC-Phe had been used, and BOC-Gly was used when BOC-(OBzl)Ser had been used: k(415)=0.30; Arg(2.04), Pro(2.05), Gly(1.98), Phe(0.98), Leu(1.95).

EXAMPLES 25–103

The following examples were prepared by methods identical to the methods described above for similarly substituted peptides, and are not limitative:

25. Arg-Pro-Pro-Gly-Phe-Ser-DNal-Phe-Arg (DNal$^7$-BK): k(415)=0.37; Arg(2.09), Pro(2.02), Gly(0.98), Phe(2.06), Ser(0.96), Nal(0.95).
26. Arg-Pro-Pro-Gly-Phe-Ser-MDY-Phe-Arg (MDY$^7$-BK): k(1:1)=4.88; Arg(2.10), Pro(1.91), Gly(0.96), Phe(2.08), Ser(0.94), MDY(1.04).
27. Arg-Pro-Pro-Gly-Phe-Ser-DPhg-Phe-Arg (DPhg$^7$-BK): k(1:1)=3.55; Arg(2.01), Pro(1.90), Gly(1.03), Phe(2.07), Ser(0.99), Phg(0.98).
28. Arg-Pro-Pro-Gly-Phe-Ser-DHis-Phe-Arg (DHis$^7$-BK): k(1:1)=0.30; Arg(2.04), Pro(2.09), Gly(0.94), Phe(2.00), Ser(1.00), His(0.93).
29. Arg-Pro-Pro-Gly-Phe-Ser-DTrp-Phe-Arg (DTrp$^7$-BK): k(415)=0.30; Arg(2.04), Pro(1.95), Gly(1.02), Phe(2.05), Ser(0.95), Trp(0.98).
30. Arg-Pro-Pro-Gly-Phe-Ser-DTyr-Phe-Arg (DTyr$^7$-BK): k(1:1)=2.70; Arg(1.94), Pro(1.88), Gly(1.04), Phe(2.10), Ser(0.97), Tyr(1.08).
31. Arg-Pro-Pro-Gly-Phe-Ser-DhPhe-Phe-Arg (DhPhe$^7$-BK): k(415)=0.37; Arg(1.99), Pro(1.94), Gly(0.97), Phe(2.02), Ser(0.88), hPhe(1.20).
32. Arg-Pro-Pro-Gly-Phe-DPhe-DThi-Phe-Arg (DPhe$^6$DThi$^7$-BK): k(415)=0.59; Arg(2.14), Pro(1.87), Gly(1.00), Phe(3.01), Thi(0.98).
33. Arg-Pro-Pro-Gly-Phe-DThi-DThi-Phe-Arg (DThi$^{6,7}$-BK): k(415)=0.54; Arg(2.04), Pro(2.00), Gly(1.01), Phe(2.04), Thi(1.91).
34. Arg-Pro-Pro-Gly-Phe-DPhe-DNal-Phe-Arg (DPhe DNal-BK): k(415)=1.04; Arg(2.02), Pro(2.04), Gly(1.01), Phe(2.94), Nal(0.99).
35. Arg-Pro-Pro-Gly-Phe-DPhe-MDY-Phe-Arg (DPhe$^6$MDY$^7$-BK): k(415)=0.59; Arg(2.11), Pro(1.90), Gly(0.97), Phe(3.02), MDY(1.01).
36. Arg-Pro-Pro-Gly-Phe-DPhe-DPal-Phe-Arg (DPhe$^6$DPal$^7$-BK): k(415)=0.16; Arg(1.86), Pro(2.12), Gly(1.07), Phe(2.90), Pal(1.05).
37. Arg-Pro-Pro-Gly-Phe-Gly-DVal-Phe-Arg (Gly$^6$DVal$^7$-BK): k(415)=0.20; Arg(2.08), Pro(2.00), Gly(1.96), Phe(1.98), Val(0.98).
38. Arg-Hyp-Pro-Gly-Phe-Ser-DPhe-Phe-Arg (Hyp$^2$DPhe$^7$-BK): k(1:1)=3.76; Arg(2.00), Pro(0.93), Gly(1.02), Phe(3.16), Ser(0.94), Hyp(0.94).
39. Arg-Pro-Hyp-Gly-Phe-Ser-DPhe-Phe-Arg (Hyp$^3$DPhe$^7$-BK): k(1:1)=3.35; Arg(1.96), Pro(0.97), Gly(1.01), Phe(3.10), Ser(0.94), Hyp(1.02).
40. Arg-Hyp-Hyp-Gly-Phe-Ser-DPhe-Phe-Arg (Hyp$^{2,3}$DPhe$^7$-BK): k(1:1)=2.33; Arg(2.03), Gly(1.02), Phe(3.10), Ser(0.94), Hyp(1.91).
41. Arg-Pro-Pro-Gly-Thi-DPhe-Thi-Arg (Thi$^{5,8}$DPhe$^{6,7}$-BK).
42. Arg-Pro-Pro-Gly-Thi-DThi-DThi-Thi-Arg (Thi$^{5,8}$DThi$^{6,7}$-BK): k(415)=0.37; Arg(2.08), Pro(2.08), Gly(0.99), Thi(3.86).
43. Arg-Pro-Pro-Gly-Thi-DThi-DPal-Thi-Arg (Thi$^{5,8}$DThi$^6$DPal$^7$-BK): k(1:1)=0.70; Arg(1.93), Pro(2.11), Gly(1.08), Thi(2.86), Pal(1.02).
44. Arg-Pro-Pro-Gly-Thi-DThi-DNal-Thi-Arg (Thi$^{5,8}$DThi$^6$DNal$^7$-BK): k(415)=0.59; Arg(2.19), Pro(2.08), Gly(1.00), Nal(0.93), Thi(2.88).
45. Arg-Pro-Pro-Gly-Thi-DThi-CDF-Thi-Arg (Thi$^{5,8}$DThi$^6$CDF$^7$-BK): k(415)=0.54; Arg(2.16), Pro(1.97), Gly(1.00), PCF(1.06), Thi(2.81).
46. Arg-Pro-Pro-Gly-Thi-DPhe-DAla-Thi-Arg (Thi$^{5,8}$DPhe$^6$DAla$^7$-BK): k(415)=0.32; Arg(2.06), Pro(1.89), Gly(0.97),Phe(1.02), Ala(0.96), Thi(2.12).
47. Arg-Pro-Pro-Gly-Thi-CDF-DAla-Thi-Arg (Tthi$^{5,8}$CDF$^6$DAla$^7$-BK): k(415)=0.39; Arg(1.96), Pro(1.93), Gly(1.00), Ala(0.99), Thi(2.05), PCF(1.08).
48. Thi-Arg-Pro-Pro-Gly-Thi-Ser-DPhe-Thi-Arg (Thi$^0$-Thi$^{5,8}$-DPhe$^7$-BK): k(415)=0.27; Arg(2.16), Pro(1.89), Gly(1.03), Phe(1.04), Ser(0.93), Thi(2.95).
49. DArg-Arg-Pro-Pro-Gly-Phe-Ser-DPhg-Phe-Arg (DArg$^0$-DPhg$^7$-BK): k(1:1)=2.03; Arg(3.05), Pro(2.00), Gly(0.97), Phe(2.04), Ser(0.94), Phg(1.00).
50. DArg-Arg-Pro-Pro-Gly-Phe-Ser-DTrp-Phe-Arg (DArg$^0$-DTrp$^7$-BK): k(1:1)=4.88; Arg(3.07), Pro(1.99), Gly(1.00), Phe(2.04), Ser(0.89), Trp(0.97).
51. DArg-Arg-Pro-Pro-Gly-Phe-Ser-DTyr-Phe-Arg (DArg$^0$-DTyr$^7$-BK): k(1:1)=1.56; Arg(2.96), Pro(2.09), Gly(1.03), Phe(1.99), Ser(0.90), Tyr(1.04).
52. DArg-Arg-Pro-Pro-Gly-Phe-Ser-DHis-Phe-Arg (DArg$^0$-DHis$^7$-BK): k(1:1)=0.18; Arg(3.08), Pro(1.99), Gly(1.02), Phe(2.07), Ser(0.89), His(0.96).
53. DArg-Arg-Pro-Pro-Gly-Phe-Ser-DhPhe-Phe-Arg (DArg$^0$-DhPhe$^7$-BK): k(415)=0.18; Arg(3.06), Pro(1.98), Gly(0.95), Phe(2.05), Ser(0.86), DhPhe(1.11).
54. Lys-Lys-Arg-Pro-Pro-Gly-Phe-Ser-DPhe-Phe-Arg (Lys-Lys-DPhe$^7$-BK: k(1:1)=0.52; Arg(2.04), Pro(2.01), Gly(0.96, Phe(3.00), Ser(0.96).
55. Lys-Lys-Arg-Pro-Pro-Gly-Phe-Ser-DTrp-Phe-Arg (Lys-Lys-DTrp$^7$-BK): k(1:1)=0.67; Arg(2.01), Pro(2.00), Gly(1.01), Phe(2.03), Ser(0.91), Trp(0.88), Lys(2.03).
56. Lys-Lys-Arg-Pro-Pro-Gly-Phe-Ser-DTyr-Phe-Arg (Lys-Lys-DTyr$^7$-BK): k(1:1)=0.21; Arg(2.01), Pro(2.11), Gly(0.99), Phe(2.02), Ser(0.97), Tyr(1.02), Lys(1.90).

57. Lys-Lys-Arg-Pro-Pro-Gly-Phe-Ser-DHis-Phe-Arg (Lys-Lys-DHis$^7$-BK): k(1:1)=0.08; Arg(1.91), Pro(2.06), Gly(0.94), Phe(2.08), Ser(0.93), His(0.95), Lys(2.12).

58. Lys-Lys-Arg-Pro-Pro-Gly-Phe-Ser-DhPhe-Phe-Arg (Lys-Lys-DhPhe$^7$-BK: k(1:1)=1.13; Arg(1.99), Pro(1.93), Gly0.98), Phe(2.06), Ser(0.92), DhPhe(1.11), Lys(2.01).

59. Arg-Pro-DPro-Gly-Phe-Ser-DPhe-Phe-Arg (DPro$^3$DPhe$^7$-BK): k(415)=0.27; Arg(2.07), Pro(1.97), Gly(0.98), Phe(3.02), Ser(0.95).

60. Arg-Pro-DPro-Gly-Phe-CDF-DAla-Phe-Arg (DPro$^3$CDF$^6$DAla$^7$-BK): k(415)=0.59; Arg(1.99), Pro(2.03), Gly(0.97), Phe(2.02), Ala(0.99), PCF(1.02).

61. Arg-Pro-DPro-Gly-Thi-Ser-DPhe-Thi-Arg (DPro$^3$Thi$^{5,8}$DPhe$^7$-BK): k(415)=0.22; Arg(2.10), Pro(1.96), Gly(1.05), Phe(0.98), Ser(0.94), Thi(1.96).

62. DArg-Arg-Pro-Pro-Gly-Thi-DPhe-DAla-Thi-Arg (DArg$^0$-Thi$^{5,8}$DPhe$^6$DAla$^7$-BK): k(1:1)=4.00; Arg(2.89), Pro(1.95), Gly(1.03), Phe(0.98), Ala(1.01), Thi(2.14).

63. DArg-Arg-Pro-Pro-Gly-Thi-CDF-DAla-Thi-Arg (DArg$^0$-Thi$^{5,8}$CDF$^6$DAla$^7$-BK): k(415)=0.19; Arg(3.00), Pro(1.99), Gly(1.00), Ala(0.96), Thi(2.03), PCF(1.02).

64. DArg-Arg-Hyp-Pro-Gly-Thi-Ser-DPhe-Thi-Arg (DArg$^0$Hyp$^2$Thi$^{5,8}$-DPhe$^7$-BK): k(1:1)=1.50; Arg(3.11), Pro(0.97), Gly(1.03), Phe(1.04), Ser(0.95), Thi(1.88), Hyp(1.02).

65. DArg-Arg-Hyp-Hyp-Gly-Thi-Ser-DPhe-Thi-Arg (DArg$^0$-Hyp$^{2,3}$Thi$^{5,8}$DPhe$^7$-Bk): k(1:1)=0.96; Arg(3.19), Gly(0.97), Phe(0.98), Ser(1.00), Thi(1.95), Hyp(1.90).

66. Thi-Arg-Hyp-Pro-Gly-Thi-Ser-DPhe-Thi-Arg (Thi$^0$-Hyp$^2$Thi$^{5,8}$DPhe$^7$-BK).

67. Thi-Arg-Pro-Hyp-Gly-Thi-Ser-DPhe-Thi-Arg (Thi$^0$-Hyp$^3$Thi$^{5,8}$DPhe$^7$-Bk).

68. Thi-Arg-Hyp-Hyp-Gly-Thi-Ser-Thi-Ser-DPhe-Thi-Arg (Thi$^0$-Hyp$^{2,3}$Thi$^{5,8}$DPhe$^7$-Bk).

69. Arg-Hyp-Pro-Gly-Thi-DPhe-CDF-Thi-Arg (Hyp$^2$-Thi$^{5,8}$-DPhe$^6$CDF$^7$-BK): k(415)=1.04; Arg(2.02), Pro(1.01), Gly(1.00), Phe(1.01), PCF(1.09), Thi(1.89), Hyp(0.98).

70. Arg-Pro-Hyp-Gly-Thi-DPhe-CFD-Thi-Arg (Hyp$^3$-Thi$^{5,8}$DPhe$^6$CDF$^7$-BK): k(1:1)=0.96; Arg(2.01), Pro(1.11), Gly(0.97), Phe(1.06), Thi(1.86), PCF(1.06), Hyp(0.95).

71. Arg-Hyp-DPro-Gly-Thi-DPhe-CDF-Thi-Arg (Hyp$^2$DPro$^3$Thi$^{5,8}$DPhe$^6$CDF$^7$-BK).

72. Lys-Lys-Arg-Hyp-Pro-Gly-Phe-Ser-DPhe-Phe-Arg (Lys-Lys-Hyp$^2$DPhe$^7$-BK): k(1:1)=0.37; Arg(1.99), Pro(0.96), Gly(0.99), Phe(3.13), Ser(0.94), Hyp(0.98), Lys(2.00).

73. Lys-Lys-Arg-Hyp-Hyp-Gly-Phe-Ser-DPhe-Phe-Arg (Lys-Lys-Hyp$^{2,3}$DPhe$^7$-Bk): k(1:1)=0.28; Arg(2.03), Gly(0.95), Ser(0.94), Phe(3.08), Lys(2.08), Hyp(1.92).

74. Lys-Lys-Arg-Pro-Pro-Gly-Thi-Ser-DThi-Thi-Arg (Lys-Lys-Thi$^{5,8}$DThi$^7$-BK): k(1:1)=0.22; Arg(2.07), Pro(2.01), Gly(1.04), Ser(0.89), Thi(3.02), Lys(1.96).

75. Lys-Lys-Arg-Pro-Pro-Gly-Thi-Ser-DPal-Thi-Arg (Lys-Lys-Thi$^{5,8}$DPal$^7$-BK): k(1:1)=0.06; Arg(2.12), Pro(1.94), Gly(1.01), Ser(0.87), Thi(1.81), Pal(0.98), Lys(2.22).

76. Lys-Lys-Arg-Pro-Pro-Gly-Thi-DPhe-CDF-Thi-Arg (Lys-Lys-Thi$^{5,8}$DPhe$^6$CDF$^7$-Bk): k(415)=0.11; Arg(2.02), Pro(2.00), Gly(1.02), Phe(1.00), PCF(1.06), Thi(1.85), Lys(2.06).

77. Lys-Lys-Arg-Pro-Hyp-Gly-Thi-Ser-DPhe-Thi-Arg (Lys-Lys-Hyp$^3$Thi$^{5,8}$DPhe$^7$-BK): k(1:1)=0.22; Arg(2.05), Pro(0.96), Gly(1.04), Phe(1.03), Ser(0.94), Hyp(1.10), Thi(1.84), Lys(2.04).

78. Lys-Lys-Arg-Hyp-Hyp-Gly-Thi-Ser-DPhe-Thi-Arg (Lys-Lys-Hyp$^{2,3}$Thi$^{5,8}$DPhe$^7$-BK): k(1:1)=0.15; Arg(2.00), Pro(2.06), Gly(1.01), Phe(1.03), Ser(0.94), Thi(1.92), Hyp(2.04).

79. Lys-Lys-Arg-Hyp-Pro-Gly-Thi-DPhe-CDF-Thi-Arg (Lys-Lys-Hyp$^2$Thi$^{5,8}$DPhe$^6$CDF$^7$-Bk): k(1:1)=6.69; Arg(1.96), Pro(1.14), Gly(0.96), Phe(1.03), Thi(1.77), PCF(1.06), Lys(1.93), Hyp(1.14).

80. Lys-Lys-Arg-Pro-Hyp-Gly-Thi-DPhe-CDF-Thi-Arg (Lys-Lys-Hyp$^3$Thi$^{5,8}$DPhe$^6$CDF$^7$-BK): k(1:1)=6.14; Arg(2.04), Pro(0.97), Gly(1.01), Phe(0.98), PCF(1.06), Thi(1.89), Hyp(1.01), Lys(2.05).

81. Lys-Lys-Arg-Hyp-Hyp-Gly-Thi-DPhe-CDF-Thi-Arg (Lys-Lys-Hyp$^{2,3}$Thi$^{5,8}$-DPhe$^6$CDF$^7$-Bk): k(1:1)=4.88; Arg(2.02), Gly(0.99), Phe(0.96), PCF(1.10), Thi(1.84), Hyp(2.01), Lys(2.06).

82. Arg-Thz-Pro-Gly-Thi-Ser-DPhe-Thi-Arg (Thz$^2$Thi$^{5,8}$DPhe$^7$-BK): k(415)=0.24; Arg(1.97), Pro(1.04), Gly(1.02), Phe(1.06), Thi(1.91).

83. Arg-Pro-Thz-Gly-Thi-Ser-DPhe-Thi-Arg (Thz$^3$Thi$^{5,8}$DPhe$^7$-BK): k(1:1)=5.25.

84. Arg-Thz-Thz-Gly-Thi-Ser-DPhe-Thi-Arg (Thz$^{2,3}$Thi$^{5,8}$DPhe$^7$-BK): K(1:1)=6.69.

85. Arg-Aib-Pro-Gly-Thi-Ser-DPhe-Thi-Arg (Aib$^2$-Thi$^{5,8}$DPhe$^7$-BK): k(415)=0.18.

86. Arg-Pro-Aib-Gly-Thi-Ser-DPhe-Thi-Arg (Aib$^3$-Thi$^{5,8}$DPhe$^7$-BK): k(415)=0.24; Arg(2.09), Pro(0.99), Gly(1.05), Ser(0.95), Phe(1.07), Thi(1.94), Aib(0.91).

87. Arg-Aib-Aib-Gly-Thi-Ser-DPhe-Thi-Arg (Aib$^{2,3}$-Thi$^{5,8}$DPhe$^7$-BK): k(415)=4.00.

88. Arg-Azt-Pro-Gly-Thi-Ser-DPhe-Thi-Arg (Azt$^2$-Thi$^{5,8}$DPhe$^7$-BK): k(415)=0.18; Arg(2.07), Pro(0.99), Gly(1.02), Phe(1.04), Ser(0.95), Thi(1.97), Azt(0.99).

89. Arg-Pro-Azt-Gly-Thi-Ser-DPhe-Thi-Arg (Azt$^3$-Thi$^{5,8}$DPhe$^7$-BK).

90. Arg-Azt-Azt-Gly-Thi-Ser-DPhe-Thi-Arg (Azt$^{2,3}$-Thi$^{5,8}$DPhe$^7$-BK).

91. Arg-Inip-Pro-Gly-Thi-Ser-DPhe-Thi-Arg (Inip$^2$-Thi$^{5,8}$-DPhe$^7$-BK): k(415)=0.21.

92. Arg-Pro-Inip-Gly-Thi-Ser-DPhe-Thi-Arg (Inip$^3$-Thi$^{5,8}$Dphe$^7$-BK): k(415)=0.18; Arg(2.10), Pro(0.95), Gly(1.04), Phe(1.03), Ser(0.93), Thi(1.95).

93. Arg-Inip-Inip-Gly-Thi-Ser-DPhe-Thi-Arg (Inip$^{2,3}$-Thi$^{5,8}$DPhe$^7$-BK): k(415)=0.18.

94. Arg-Pro-Pro-Gly-Thi-Ser-DNal-Thi-Arg (Thi$^{5,8}$D-Nal$^7$-BK): k(415)=0.32.

95. Arg-Pro-Pro-Gly-Thi-Ser-CDF-Thi-Arg (Thi$^{5,8}$CDF$^7$-BK): k(415)=0.28.

96. Arg-Pro-Pro-Gly-Thi-Ser-DTyr-Thi-Arg (Thi$^{5,8}$-DTyr$^7$-BK): k(4.15)=0.12.

97. Arg-Pro-Pro-Gly-Thi-Ser-DVal-Thi-Arg (Thi$^{5,8}$D-Val$^7$-BK): k(415)=0.11.

98. Arg-Pro-Pro-Gly-Thi-Ser-DIle-Thi-Arg (Thi$^{5,}$sDIle$^7$-BK): k(415)=0.16.

99. Arg-Pro-Pro-Gly-Thi-Ser-DLeu-Thi-Arg (Thi$^{5,8}$-DLeu$^7$-BK).

100. Arg-Pro-Pro-Gly-Thi-Ser-DTrp-Thi-Arg (Thi$^{5,8}$DTrp$^7$-BK).

101. Arg-Pro-Pro-Gly-Thi-Ser-DPhg-Thi-Arg (Thi$^{5,8}$DPhg$^7$-BK).

102. Arg-Pro-Pro-Gly-Thi-Ser-DHis-Thi-Arg (Thi$^{5,8}$DHis$^7$-BK).

103. Arg-Pro-Pro-Gly-Thi-Ser-DOMT-Thi-Arg (Thi$^{5,}$ $^8$DOMT$^7$-BK): k(415)=0.18.

EXAMPLES OF BRADYKININ ANTAGONIST ACTIVITY

The bradykinin antagonists were assayed on isolated rat uterus in natural or induced estrus and on guinea pig ileum, according to the commonly accepted assay methods for bradykinin and related kinins as described by Trautschold (Handbook of Expt. Pharmacol. Vol. 25, Springer Verlag, pp 53-55, 1970) for inhibition of the myotropic activity of bradykinin. The inhibition potencies, as determined according to the commonly accepted manner described by Schild for antagonists of biologically active compounds (Br. J. Pharmacol. 2:189, 1947), are determined on isolated rat uterus (RUT) and isolated guinea pig ileum (GPI). In the assays, a dose-response curve is determined for the reference substance bradykinin. The dose of bradykinin which produced a half maximal contraction of tissue is the ED50 dose. An amount of bradykinin equivalent to twice the ED50 dose is administered to the tissue 30 seconds after the start of incubation of the tissue with a dose of antagonist. Doses of antagonist are increased in this protocol until pre-incubation with a dose of antagonist reduces the contraction in response to the double ED50 dose of bradykinin to response of a single ED50 dose of bradykinin. The pA2 value represents the negative logarithm of the molar concentration of antagonist necessary to reduce the response of a double ED50 dose of bradykinin to that of an ED50 dose. One unit of pA2 value represents an order of magnitude change in potency. For comparison, the negative log of the dose of BK, the dose which causes half maximal contraction of the tissues, is commonly known as the pD2 value. The pD2 value for bradykinin is 7.9 on the rat uterus and 7.4 on the guinea pig ileum.

POTENCY OF BRADYKININ ANTAGONISTS

| EXAMPLE # | STRUCTURE | pA2/RUT | pA2/GPI |
|---|---|---|---|
| 1 | DPhe$^7$—BK | | 5.0 |
| 2 | DThi$^7$—BK | | 4.6 |
| 3 | DPal$^7$—BK | 5.0 | 4.8 |
| 4 | DPhe$^{6,7}$—BK | | 5.2 |
| 5 | DPhe$^6$CDF$^7$—BK | 4.9 | 5.8 |
| 6 | Thi$^{5,8}$DPhe$^7$—BK | 6.5 | 6.3 |
| 7 | Thi$^{5,8}$DThi$^7$—BK | 4.2 | 5.8 |
| 8 | Thi$^{5,8}$DPal$^7$—BK | 4.2 | |
| 10 | DArg$^0$—DPhe$^7$—BK | | 5.6 |
| 11 | DArg$^0$—DPro$^3$DPhe$^7$—BK | 4.0 | |
| 13 | Lys—Lys—DPhe$^7$—BK | | 5.1 |
| 14 | Lys—Lys—Thi$^{5,8}$DPhe$^7$—BK | 6.0 | 5.3 |
| 15 | DArg$^0$—Thi$^{5,8}$DPhe$^7$—BK | 5.5 | 6.1 |
| 16 | DArg$^0$—DPro$^3$Thi$^{5,8}$DPhe$^7$—BK | 5.2 | |
| 18 | Hyp$^2$Thi$^{5,8}$DPhe$^7$—BK | 5.6 | |
| 19 | Lys—Lys—Hyp$^2$Thi$^{5,8}$DPhe$^7$—BK | 5.8 | |
| 20 | Hyp$^3$Thi$^{5,8}$DPhe$^7$—BK | 7.0 | 4.7 |
| 21 | DArg$^0$—Hyp$^3$Thi$^{5,8}$DPhe$^7$—BK | 7.2 | |
| 22 | Hyp$^{2,3}$Thi$^{5,8}$DPhe$^7$—BK | 6.7 | |
| 23 | Hyp$^{2,3}$Thi$^{5,8}$DPhe$^6$CDF$^7$—BK | 6.5 | |
| 64 | DArg$^0$—Hyp$^2$Thi$^{5,8}$DPhe$^7$—BK | 5.7 | |
| 65 | DArg$^0$—Hyp$^{2,3}$Thi$^{5,8}$DPhe$^7$—BK | 7.1 | |
| 72 | Lys—Lys—Hyp$^2$DPhe$^7$—BK | 5.6 | |
| 77 | Lys—Lys—Hyp$^3$Thi$^{5,8}$DPhe$^7$—BK | 6.7 | |

EXAMPLE OF SPECIFICITY OF KININ ANTAGONISM ON SMOOTH MUSCLE

The specificity of bradykinin antagonists of this invention is demonstrated by their ability to inhibit the myotropic activity of bradykinin (BK) and two physiologically important BK-related kinins, kallidin (KAL, Lys-BK) and methionyl-lysyl-BK (MK-BK), but not the myotropic activity induced by non kinin-related peptides, such as angiotensin-II (ANG) or substance-P (SP). In each case, as shown, the BK-related antagonists inhibited contractions produced by BK-related agonists, but had no effect on the non-kinin myotropic peptide substances. The inhibition potencies are listed as pA2 values as described above.

SPECIFICITY OF BRADYKININ ANTAGONISTS IN GUINEA PIG ILEUM ASSAY

| EXAMPLE # | STRUCTURE | GUINEA PIG ILEUM | | | | |
|---|---|---|---|---|---|---|
| | | BK | KAL | MK—BK | ANG | SP |
| 1 | DPhe$^7$—BK | 5.0 | 5.6 | 6.0 | NO | NO |
| 6 | Thi$^{5,8}$DPhe—BK | 6.3 | 6.4 | 5.2 | NO | NO |
| 10 | DArg$^0$—DPhe$^7$—BK | 5.6 | 6.0 | 6.3 | NO | NO |
| 15 | DArg$^0$—Thi$^{5,8}$DPhe$^7$—BK | 6.1 | 6.7 | 6.4 | NO | NO |

EXAMPLE OF THE ANTAGONISM OF BRADYKININ ANTAGONISTS ON RAT BLOOD PRESSURE

The in vivo effects of bradykinin antagonists on blood pressure in the anesthetized rat are determined according to the assay described by Roblero, Ryan and Stewart (Res. Commun. Pathol. Pharmacol. 6:207, 1973). When compounds #6 (Thi$^{5,8}$DPhe$^7$-BK), #10 (DArg$^0$-DPhe$^7$-BK) and #15 (DArg$^0$-Thi$^{5,8}$DPhe$^7$-BK) are infused at a rate of 25 μg/min, the response to a 25 mm depressor dose (ED25 mm) of bradykinin is reduced from 25 mm to 10 mm. The depressor effect of bradykinin returns to a normal response within 5 minutes of terminating the infusion of antagonist. The antagonists also produce inhibition of the bradykinin response when injected as a bolus admixture of bradykinin plus antagonist by either the ia or iv route of administration.

EXAMPLES OF CONFERRING RESISTANCE TO ENZYMATIC DEGRADATION BY EXTENSION AT THE N-TERMINAL OF BRADYKININ ANALOG

The ability of bradykinin analogs to withstand enzymatic degradation (for example by kininases) in vivo can be conveniently assessed, for example, by determining residual vasodepressor activity of a particular analog after a single pass in the pulmonary circulation in the anesthetized rat (J. Roblero, J. W. Ryan, and J. M.

Stewart, Res. Commun. Pathol. Pharmacol. 6:207, 1973) following intraaortic and intravenous administration. In this system, using N-terminal substituted bradykinin analogs (agonists), the following results are obtained:

| RAT PULMONARY DESTRUCTION OF BK ANALOGS MODIFIED AT THE N-TERMINAL | |
|---|---|
| PEPTIDE STRUCTURE | % DESTRUCTION |
| Bradykinin (BK) | 98 |
| Lys—BK | 95 |
| DArg—BK | 92 |
| DLys—BK | 89 |
| Lys—Lys—BK | 0 |
| Thi$^{5,8}$—BK | 95 |
| Lys—Lys—Thi$^{5,8}$—BK | 0 |

The resistance of N-terminal-extended BK analogs to kininase degradation, especially those with Lys-Lys-extensions, suggests that long-acting antagonists of BK activity would be obtained by modifying the [D-Phe$^7$]-BK inhibitors with a Lys-Lys-extension. Additionally, observations that a D-Arg residue added to the N terminal of BK agonists tends to increase uterine potency without affecting ileum activity prompted the synthesis of D-Arg- extended D-Phe$^7$ BK analogs as tissue-specific inhibitors.

N-terminal extension of D-Phe$^7$BK with Lys-Lys- or with the D-Arg residue reduced agonist potency in the uterus assay but has no effect on the antagonism seen in the ileum assay. Similarly, the inhibitory effect of Thi$^{5,8}$DPhe$^7$BK was diminished on the uterus with the addition of either Lys-Lys- or D-Arg to the N-terminal. In the ileum assay addition of D-Arg to the very potent Thi$^{5,8}$DPhe$^7$BK antagonist had little effect on inhibitory potency.

EXAMPLES OF CONFERRING TISSUE SELECTIVITY BY MODIFICATION OF BRADYKININ ANTAGONISTS AT POSITION 2 AND 3

Bradykinin agonists produced by modification of the bradykinin nonapeptide sequence exhibit similar potencies in the classic rat uterus (RUT) and guinea pig ileum (GPI) assays relative to bradykinin. Recently, dissociation of smooth muscle activities towards significantly higher uterine activity vs ileum activity has been reported in bradykinin analogs containing aminoisobutyric acid (Aib) in position 7 (R. J. Vavrek & J. M. Stewart, Peptides 1:231, 1980), and in bradykinin analogs with multiple D-amino acid substitutions in position 6 and 7 (R. J. Vavrek & J. M. Stewart, in Kinins 1984, L. M. Greenbaum, ed, Plenum Press, NY, 1985).

The addition of a D-amino acid residue to the N-terminus of the ileum-selective bradykinin antagonist D$Phe^7$-BK (i.e., DArg) does not change selectivity for inhibiting bradykinin activity on the ileum (i.e., D$Arg^0$-D$Phe^7$-BK). Modification of D$Phe^7$-BK at position 3 by the substitution of a DPro residue (i.e., D$Pro^3$D$Phe^7$-BK) eliminates antagonist activity in the ileum assay and destroys agonist activity in the uterus assay. Replacement of the Pro residue at position 3 of D$Arg^0$-D$Phe^7$-BK reverses the spectrum of smooth muscle activity towards uterine- selective antagonism, with complete loss of antagonism of bradykinin in the ileum assay. Likewise, substitution of the Pro residue at position 3 of the nonspecific antagonist D$Arg^0$$Thi^{5,8}$D$Phe^7$-BK with a DPro residue eliminates antagonism of bradykinin action on the ileum, but full antagonist activity in the uterine assay is retained.

| ANTAGONIST SPECIFICITY IN SMOOTH MUSCLE ASSAYS BY MODIFICATION OF POSITION 3 | | | |
|---|---|---|---|
| EX-AM-PLE | STRUCTURE | RUT | GPI |
| 1 | D$Phe^7$—BK | (1% AG) | $pA_2$ = 5.0 |
| 10 | D$Arg^0$—D$Phe^7$—BK | (0.1% AG) | $pA_2$ = 5.0 |
| 59 | D$Pro^3$—D$Phe^7$—BK | 0 | 0 |
| 11 | D$Arg^0$—D$Pro^3$—D$Phe^7$—BK | $pA_2$ = 4.6 | 0 |
| 15 | D$Arg^0$—$Thi^{5,8}$D$Phe^7$—BK | $pA_2$ = 5.2 | $pA_2$ = 6.1 |
| 16 | D$Arg^0$—D$Pro^3$$Thi^{5,8}$D$Phe^7$—BK | $pA_2$ = 5.2 | 0 |

AG = agonist potency relative to BK = 100. $pA_2$ is the inhibition potency as defined by Schild (Br. J. Pharmacol. 2:189, 1947).

Tissue selectivity of bradykinin analogs can also be altered by modification of the Pro at position 2. It has been found that substitutions of Val, Sar, Pro, Ala, Hyp and Aib (alpha-aminoisobutyrate) at position 2 confer differential tissue selectivity of selected bradykinin analogs in an assay of myotropic activity determined on guinea pig ileum versus rat uterus (R. J. Vavrek and J. M. Stewart, Peptides, 231-235, 1980). The tissue selectivity conferred upon various bradykinin analogs by such substitutions at position 2 suggests that similar substitution in any bradykinin analog, including those with antagonist activity, will confer tissue selectivity.

Theraputic applications of the novel bradykinin antagonists include not only treatment for the production of bradykinin or related kinins by the animal but also the injection of bradykinin related peptides into an animal as a result of bites and stings. Topical application alone or in combination with subcutaneous utilization of the bradykinin antagonists of the invention can be employed to treat the effects of bradykinin-related peptides causing pain, inflammation and swelling.

The therapeutic use of bradykinin antagonists of this invention for other traumatic, inflammatory or pathological conditions which are known to be mediated by bradykinin or exacerbated by an overproduction of bradykinin can also be achieved. These conditions include local trauma such as wounds, burns and rashes, angina, arthritis, asthma, allergies, rhinitis, shock, inflammatory bowel disease, low blood pressure, systemic treatment of pain inflammation, and low sperm motility which produces male infertility. The present bradykinin antagonists, as discussed may be advantageously administered in a variety of ways including sublingual absorption as with nitroglycerine or patch administration using agents for assisting absorption through the skin such as for the treatment of angina. Based upon the $PA_2$ and $ED_{50}$ data disclosed in this invention and in the prior art related to agonist potency, it is possible for one skilled in the art to make a determination of the dosage of the novel bradykinin antagonists of the invention.

It is therefore estimated that the dosage range for typical application in such conditions as the pain and inflammation of wound, burns and rashes would be 0.1-5 mg/ml; for a nasal spray formulation suitable for treating rhinitis, allergies and asthma suitable dosage range would be 0.1-5 mg/ml; for intravenous formulation suitable for the treatment of systemic inflammation, shock, arthritis, allergies, asthma and for increasing sperm motility, a suitable dosage range would be 0.1-10 mg/kg; for an oral formulation for the treatment of inflammatory bowel disease or general pain and inflammation a suitable dosage range would be 10-100 mg/kg.

Bradykinin antagonists can also be administered intravaginally, intrarectally, intrabuccally or any other accepted internal application.

As will be recognized by those skilled in the art the present invention has a wide range of applicability to providing competitive inhibitors to the biological activities of bradykinin produced by the body in illness, injury and shock. The advantages of the invention in substituting the L-Pro position 7 with amino acids of the D-configuration to convert bradykinin agonists to antagonists provide a wide variety of specific and competitive antagonists for reducing the known effects of bradykinin. The additional advantages of the invention of modifying the L-Pro position 7 in conjunction with modifications at the other positions of the novel bradykinin antagonists provides a variety of useful compounds. It will further be appreciated the present invention is susceptible to these and other modifications within the parameters of the invention without departing from the scope of the following claims.

What is claimed is:

1. A modified bradykinin type peptide having the formula

A-Arg-B-C-D-W-X-Y-Z-Arg and pharmaceutically acceptable salts thereof wherein
a. A is selected from the L-, D- or non configured forms of the group consisting of
  (i) hydrogen
  (ii) Arg
  (iii) Lys-Lys
  (iv) Phe
  (v) Thi
  (vi) Lys
  (vii) Met-Lys
  (viii) Gly-Arg-Met-Lys;
b. B is selected from the L-, D- or non configured forms of the group consisting of
  (i) Azetidine-2-Carboxylic acid (Azt)
  (ii) Thiazolidine-2-Carboxylic acid (Thz)
  (iii) Isonipecotic acid (Inip)
  (iv) Pro
  (v) 2,3-Dehydroproline (Δ Pro)
  (vi) 4-Hydroxyproline (Hyp)
  (vii) Aib;
c. C is selected from the L-, D- or non configured forms of the group consisting of
  (i) Azetidine-2-Carboxylic acid (Azt)
  (ii) Thiazolidine-2-Carboxylic acid (THz)
  (iii) Isonipecotic acid (Inip)
  (iv) Pro
  (v) 2,3-Dehydroproline (Δ Pro)
  (vi) 4-Hydroxyproline (Hyp)
  (vii) Aib;
d. D is selected from the L-, D- or non configured forms of the group consisting of
  (i) Gly
  (ii) Ala
  (iii) Sar;
e. W is selected from the L-, D- or non configured forms of the group consisting of
  (i) Phe
  (ii) beta-(2-Thienyl)-Alanine (Thi)
  (iii) O-Methyltyrosine (OMT)
  (iv) beta-(2-Pyridyl) Alanine (Pal)
  (v) Para-Chloro-L-Phenylalanine (CLF)
  (vi) Para-Nitrophenylalanine (PNF)
  (vii) beta-(2-Naphthyl)-Alanine (Nal)
  (viii) Leu;
f. X is selected from the L-, D- or non configured forms of the group consisting of
  (i) Ser
  (ii) Gly
  (iii) Phe
  (iv) Para-Chloro-D-phenylalanine (CDF)
  (v) Nal
  (vi) Pal
  (vii) Thi
  (viii) pCl-Phe;
g. Y is a D-configured form selected from the group consisting of
  (i) DNal
  (ii) DPNF
  (iii) DPhe
  (iv) DTyr
  (v) DPal
  (vi) DOMT
  (vii) DThi
  (viii) DAla
  (ix) DTrp
  (x) DHis
  (xi) D-Homo-Phe (DhPhe)
  (xii) pCl-DPhe (CDF)
  (xiii) DPhg
  (xiv) D-Val
  (xv) DIle
  (xvi) DLeu
  (xvii) MDY; and
h. Z is selected from the L-, D- or non configured forms of the group consisting of
  (i) Phe
  (ii) beta-(2-thienyl) alanine (Thi)
  (iii) O-methyltyrosine (OMT)
  (iv) beta-(2-pyridyl) alanine (Pal)
  (v) para-chloro-L-phenylalanine (CLF)
  (vi) para-nitrophenylalanine (PNF)
  (vii) beta-(2-naphthyl)-alanine (Nal)
  (viii) Leu.

2. The compound as defined in claim 1 wherein Y is DPhe, beta-2-thienyl-DAla (DThi), beta-2-pyridyl-DAla (DPal), beta-2-naphthyl-DAla(DNal), DHis, D-homo-Phe(DhPhe), O-methyl-DTyr(DOMT), D-alphaphenyl-Gly(DPhg), DTrp, DTyr, pNO$_2$-DPhe(PNF) or pCl-DPhe(CDF).

3. The pharmaceutical composition comprising the compounds as defined in claim 1 wherein enhanced resistance to enzymatic degradation is achieved by modifying the moiety A.

4. The pharmaceutical composition comprising the compounds as defined in claim 3 possessing enhanced resistance to enzymatic degradation wherein A is D-Arg, D-Lys, Lys-Lys, L-Thi, Met-Lys or Gly-Arg-Met-Lys and the pharmaceutically acceptable salts thereof in combination with a pharmaceutically acceptable carrier.

5. The pharmaceutical composition comprising the compounds as defined in claim 1 wherein enhanced tissue selectivity is achieved by modifying the moiety B alone or in combination with a modification of the moiety C.

6. The pharmaceutical composition comprising the compounds as defined in claim 5 possessing enhanced tissue selectivity wherein B alone, C alone or a combination thereof are selected from a group comprising L-Pro, L-hydroxyproline, Δ Pro, alphaammoisobutyric acid (Aib) and the pharmaceutically acceptable salts thereof in combination with a pharmaceutically acceptable carrier.

7. The pharmaceutical composition comprising the compounds as defined in claim 1 wherein enhanced potency is achieved by modifying the moiety W, X or Z alone or in combination.

8. The pharmaceutical composition comprising the compound as defined in claim 7 possessing enhanced potency wherein W alone or Z alone or in combination are selected from a group comprising Phe, O-Methyl-Tyr(OMT), p-Chloro-Phe(CLF), p-Nitro-Phe(PNF), beta-2-naphthyl-Ala(NAL), Thi, Pal, and the pharmaceutically acceptable salts thereof in combination with a pharmaceutically acceptable carrier.

9. The pharmaceutical preparation for treating local pain and inflammation from burns, wounds, cuts, rashes and other such trauma and pathologic conditions caused by the production of bradykinin or related kinins by the animal which comprises an effective amount of the compound of claim 1 sufficient to antagonize bradykinin and a suitable pharmaceutical carrier.

10. A process for treating local pain and inflammation which comprises administering an effective amount of the pharmaceutical preparation of claim 9 to a host.

11. The pharmaceutical preparation for treating local pain, inflammation and swelling from bites, stings or other injection of bradykinin or related kinins which comprises an effective amount of the compound of claim 1 sufficient to antagonize bradykinin and a suitable pharmaceutical carrier.

12. A process for treating local pain, inflammation and swelling which comprises administering an effective amount of the pharmaceutical preparation of claim 11 to a host.

13. The pharmaceutical preparation for treating rhinitis and other such trauma and pathologic conditions comprising an effective amount of the compound of claim 1 and a suitable pharmaceutical carrier.

14. A process for treating rhinitis which comprises administering an effective amount of claim 13 to a host.

15. The pharmaceutical preparation for treating low blood pressure and other such trauma and pathologic conditions caused by the production of bradykinin or related kinins by the animal which comprises an effective amount of the compound of claim 1 and a suitable pharmaceutical carrier.

16. A process for treating low blood pressure which comprises administering an effective amount of the pharmaceutical preparation of claim 15 to a host.

17. The pharmaceutical preparation for treating asthma and other such trauma and pathologic conditions caused by the production of bradykinin or related kinins by the animal which comprises an effective amount of the compound of claim 1 and a suitable pharmaceutical carrier.

18. A process for treating asthma which comprises administering an effective amount of the pharmaceutical preparation of claim 17 to a host.

19. The pharmaceutical preparation for treating arthritis and other such trauma and pathologic conditions caused by the production of bradykinin or related kinins by the animal which comprises an effective amount of the compounds of claim 1 and a suitable pharmaceutical carrier.

20. A process for treating arthritis which comprises administering an effective amount of the pharmaceutical preparation of claim 19 to a host.

21. The pharmaceutical preparation for treating diarrhea and other such trauma and pathologic conditions caused by the production of bradykinin or related kinins by the animal which comprises an effective amount of the compound of claim 1 and a suitable pharmaceutical carrier.

22. A process for treating diarrhea which comprises administering an effective amount of the pharmaceutical preparation of claim 21 to a host.

23. The pharmaceutical preparation for treating irritable bowel syndrome and inflammatory bowel disease and other such trauma and pathologic conditions caused by the production of bradykinin or related kinins by the animal which comprises an effective amount of the compound claim 1 and a suitable pharmaceutical carrier.

24. A process for treating irritable bowel syndrome and inflammatory bowel disease which comprises administering an effective amount of the pharmaceutical preparation of claim 23 to a host.

25. The pharmaceutical preparation for treating carcinoid syndrome and other such trauma and pathologic conditions caused by the production of bradykinin or related kinins by the animal which comprises an effective amount of the compound of claim 1 and a suitable pharmaceutical carrier.

26. A process for treating carcinoid syndrome which comprises administering an effective amount of the pharmaceutical preparation of claim 25 to a host.

27. The pharmaceutical preparation for treating pain associated with angina and other such trauma and pathologic conditions caused by the production of bradykinin or related kinins by the animal which comprises an effective amount of the compound of claim 1 and a suitable pharmaceutical carrier.

28. A process for treating pain associated with angina which comprises administering an effective amount of the pharmaceutical preparation of claim 27 to a host.

29. The pharmaceutical preparation for treating pain and inflammation caused by the production of bradykinin or related kinins by the animal which comprises an effective amount of the compound of claim 1 and a suitable pharmaceutical carrier.

30. A process for treating pain and inflammation which comprises administering an effective amount of the pharmaceutical preparation of claim 29 to a host.

31. The pharmaceutical preparation for treating anaphylactic and septic shock and other such trauma and pathologic conditions caused by bradykinin or related kinins in the animal which comprises an effective amount of the compound of claim 1 with a suitable pharmaceutical carrier.

32. A process for treating anaphylactic and septic shock which comprises administering an effective amount of the pharmaceutical preparation of claim 31 to a host.

33. The pharmaceutical preparation for increasing male fertility by increasing sperm motility which comprises an effective amount of the compound of claim 1 and a suitable pharmaceutical carrier.

34. A process for treating male fertility which comprises administering an effective amount of the pharmaceutical preparation of claim 33 to a host.

35. A modified bradykinin type peptide antagonist having the formula

A-Arg-B-C-D-W-X-Y-Z-Arg and the pharmaceutically acceptable salts thereof
wherein
a. A is selected from the L-, D- or non configured isomers of the group consisting of
 (i) hydrogen
 (ii) Arg
 (iii) Lys-Lys
 (iv) Phe
 (v) Thi
 (vi) Lys
 (viii) Met-Lys
 (ix) Gly-Arg-Met-Lys
b. B is selected from the L-, D- or non configured isomers of the group consisting of
 (i) Azetidine-2-Carboxylic Acid (Azt)
 (ii) Thiazolidine-2-Carboxylic acid (THz)
 (iii) Isonipecotic acid (Inip)
 (iv) Pro
 (v) 2,3-Dehydroproline (Δ Pro)
 vi) Hydroxyproline
 (vii) Aib
 (viii) Dehydroproline
 (ix) Val
 (x) Ala
 (xi) Sar
 (xii) Gly
c. C is selected from the L-, D- or non configured isomers of the group consisting of
 (i) Azetidine-2-Carboxylic acid (Azt)
 (ii) Thiazolidine-2-Carboxylic acid (Thz)
 (iii) Isonipecotic acid (Inip)
 (iv) Pro
 (v) 2,3-Dehydroproline (Δ Pro)
 (vi) 4-Hyroxyproline (Hyp)
 (vii) Aib
 (viii) Val
 (ix) Ala
 (x) Sar
 (xi) Gly
d. D is selected from the L-, D- or non configured isomers of the group consisting of
 (i) Gly
 (ii) Ala
 (iii) Sarcosine (Sar)
e. W is selected from the L-, D- or non configured isomers of the group consisting of
 (i) Phe
 (ii) beta-(2-Thienyl)-Alanine (Thi)
 (iii) O-Methyltyrosine (OMT)
 (iv) beta-(2-Pyridyl) Alanine (Pal)
 (v) Para-Chloro-Phenylalanine (CLF)
 (vi) Para-nitrophenylalanine (PNF)
 (vii) beta-(2-Naphthyl)-Alanine (Nal)
 (viii) Leu
 (ix) Ser
 (x) Tyr
f. X is selected from the L-, D- or non configured isomers of the group consisting of
 (i) Ser
 (ii) Gly
 (iii) Phe
 (iv) Para-Chloro-D-phenylalanine (CDF)
 (v) Nal
 (vi) Pal
 (vii) Thi
 (viii) pCl-Phe g. Y is responsible for providing antagonist activity and is a D- configured isomer selected from the group consisting of
 (i) D-aliphatic-amino acid residue
 (ii) D-Heterocyclic amino acid residue
 (iii) D-aromatic amino acid residue
 (iv) substituted D-aromatic amino acid residue
h. Z is selected from the L-, D- or non configured isomers of the group consisting of
 (i) Phe
 (ii) beta-(2-thienyl) alanine (Thi)
 (iii) O-methyltyrosine (OMT)
 (iv) beta-(2-pyridyl) alanine (Pal)
 (v) para-chloro-L-phenylalanine (CLF)
 (vi) para-nitrophenylalanine (PNF)
 (vii) beta-(2-naphthyl)-alanine (Nal)
 (viii) Leu
 (ix) Tyr
i. Arg is Arginine of the D- or L-configuration.

36. A pharmaceutical preparation comprising a suitable pharmaceutical carrier and an effective amount of a modified bradykinin type peptide antagonist having the formula A-Arg-B-C-D-W-X-Y-Z-Arg and the pharmaceutically acceptable salts thereof
wherein
a. A is L-, D- or non configured and is selected from the group consisting of
 (i) hydrogen
 (ii) Arg
 (iii) Lys-Lys
 (iv) Phe
 (v) Thi
 (vi) Lys
 (vii) Met-Lys
 (viii) Gly-Arg-Met-Lys
b. B is L-, D- or non configured and is selected from the group consisting of
 (i) Azetidine-2-Carboxylic Acid (Azt)
 (ii) Thiazolidine-2-Carboxylic acid (THz)
 (iii) Isonipecotic acid (Inip)
 (iv) Pro
 (v) 2,3-Dehydroproline (Δ Pro)
 (vi) 4-Hydroxyproline (Hyp)
 (vii) Aib
 (viii) Val
 (ix) Ala
 (x) Sar
 (xi) Gly
c. C is L-, D- or non configured and is selected from the group consisting of
 (i) Azetidine-2-Carboxylic acid (Azt)
 (ii) Thiazolidine-2-Carboxylic acid (THz)
 (iii) Isonipecotic acid (Inip)
 (iv) Pro
 (v) 2,3-Dehydroproline (Δ Pro)
 (vi) 4-Hydroxyproline (Hyp)
 (vii) Aib
 (viii) Val
 (ix) Ala
 (x) Sar
 (xi) Gly
d. D is L-, D- or non configured and is selected from the group consisting of
 (i) Gly
 (ii) Ala (iii) Sarcosine (Sar)
e. W is L-, D- or non configured and is selected from the group consisting of
  (i) Phe
  (ii) beta-(2 Thienyl)-Alanine (THi)
  (iii) O-Methyltyrosine (OMT)
  (iv) beta-(2-Pyridyl) Alanine (Pal)
  (v) Para-Chloro-L-Phenylalanine (CLF)
  (vi) Para-nitrophenylalanine (PNF)
  (vii) beta-(2-Naphthyl)-Alanine (Nal)
  (viii) Leu
  (ix) Ser
  (x) Tyr
f. X is L-, D- or non configured and is selected from the group consisting of
  (i) Ser
  (ii) Gly
  (iii) Phe
  (iv) Para-Chloro-D-phenylalanine (CDF)
  (v) NAL
  (vi) Pal
  (vii) Thi
  (viii) pCl-Phe
g. Y is the D-form and is selected from the group consisting of
  (i) D-aromatic amino acid residue
  (ii) substituted D-aromatic amino acid residue
  (iii) D-aliphatic amino acid residue
  (iv) D-heterocyclic amino acid residue
h. Z is L-, D- or non configured and is selected from the group consisting of
  (i) Phe
  (ii) beta-(2-thienyl) alanine (THi)
  (iii) O-methyltyrosine (OMT)
  (iv) beta-(2-pyridyl) alanine (Pal)
  (v) para-chloro-L-phenylalanine (CLF)
  (vi) para-nitrophenylalanine (PNF)
  (vii) beta-(2-naphthyl)-alanine (Nal)
  (viii) Leu
  (ix) Tyr.

37. A process for treating low blood pressure, asthma, arthritis, diarrhea, irritable bowel syndrome and inflammatory bowel disease, carcinoid syndrome, pain associated with angina, anaphylactic and septic shock caused by the production of bradykinin by an animal comprising administering to a host the pharmaceutical preparation of claim 36.

38. The pharmaceutical preparation of claim 36 wherein Y is selected from the group consisting of DPhe, DThi, DPal, CDF, DNal, MDY, DPhg, DHis, DTrp, DTyr, DhPhe, DVal, DAla, DIle, DLeu, and DOMT.

* * * * *